United States Patent [19]

Royer

[11] 3,930,950
[45] Jan. 6, 1976

[54] METHOD OF IMMOBILIZING AN ENZYME

[75] Inventor: Garfield P. Royer, Worthington, Ohio

[73] Assignee: The Ohio State University Research Foundation, Columbus, Ohio

[22] Filed: Apr. 9, 1974

[21] Appl. No.: 459,300

[52] U.S. Cl. ............. 195/63; 195/68; 195/DIG. 11
[51] Int. Cl.² ............................................ C07G 7/02
[58] Field of Search ........... 195/62, 63, 68, DIG. 11

[56] References Cited
UNITED STATES PATENTS
3,802,997   4/1974   Messing ................................. 195/68

Primary Examiner—Lionel M. Shapiro
Attorney, Agent, or Firm—Sidney W. Millard

[57] ABSTRACT

A method of immobilizing an enzyme is presented which comprises (1) providing an active support member which is capable of reacting with an enzyme to thereby cause the enzyme to become chemically bonded thereto and (2) contacting the active support member with an enzyme-substrate complex which has been formed by mixing together an enzyme and a specific substrate while minimizing the transformation of the substrate to product, whereby the enzyme component of the enzyme-substrate complex becomes chemically bonded to the support member. Subsequently, the substrate is removed from the enzyme-substrate complex by conventional means, such as water washing, thereby leaving the active enzyme chemically bonded to the support member.

16 Claims, No Drawings

METHOD OF IMMOBILIZING AN ENZYME

BACKGROUND OF THE INVENTION

This invention relates to an improved method of immobilizing enzymes. More specifically, it concerns a method of immobilizing enzymes by a technique which includes the formation of an enzyme-substrate complex, the bonding of the enzyme portion of the enzyme-substrate complex to an active support member, and the subsequent removal of the substrate from the so-bonded enzyme.

PRIOR ART

Many chemical reactions, especially those occurring in living organisms, are accelerated by enzymes. Generally, the reaction catalyzed by an enzyme would proceed with extreme slowness in the absence of the enzyme. In other words, an enzyme is a chemical substance which is capable oof accelerating certain chemical reactions. In the art, those substances which undergo a chemical reaction due to the catalytic action of an enzyme are called substrates.

In many commercial processes where enzymes are employed, the enzyme is not recoverable due to the fact that it is either removed with the desired product or lost in a subsequent cleaning or purification operation. In order to overcome this difficulty, it has become well known in the art to chemically bond the enzyme to an insoluble support member so that it is not lost during the concerned process. Various support members for bonding enzymes thereto are well known in the art. In fact, the art is replete with various techniques for bonding a given enzyme to a support member. In general, such techniques simply require that the desired enzyme be brought into contact with an active support member. While such prior art immobilizing techniques result in a more efficient utilization of the concerned enzyme they are generally characterized by certain inherent inefficiencies. For example, generally, the so-bonded enzyme exhibits a significantly reduced degree of activity. In addition, often times the enzyme is substantially damaged during the bonding procedure which, obviously, results in either an ineffective enzyme or one which exhibits a significantly reduced degree of activity.

Accordingly, it is the primary object of the instant invention to provide a method for immobilizing an enzyme by chemically bonding it to a suitable support member in such a manner that the bonded enzyme exhibits a higher degree of activity than it would have exhibited had it been bonded to the support member by conventional techniques.

An additional object of the instant invention is to provide a method of immobilizing an enzyme by bonding it to a support member without significantly damaging the enzyme during the bonding or immobilizing procedure.

Additional objects of the invention will become apparent to those skilled in the art from a reading of the subject application and appended claims.

SUMMARY OF THE INVENTION

A method of immobilizing an enzyme is provided which comprises providing an active support member which is capable of reacting with an enzyme to thereby cause the enzyme to become chemically bonded thereto and then contacting the active support member with an enzyme-substrate complex which has been formed by mixing together an enzyme and a specific substrate while minimizing the transformation of the substrate to product, whereby the enzyme component of the enzyme-substrate complex becomes chemically bonded to the support member. Subsequently, if desired, the substrate is removed from the enzyme-substrate complex by conventional means, such as water washing, with the resultant product being an active enzyme which is chemically bonded to the support member.

DESCRIPTION OF THE PREFERRED EMBODIMENTS OF THE INVENTION

In the preferred practice of the invention an enzyme is immobilized by a method which includes (1) providing an active support member which is capable of reacting with the enzyme thereby causing the enzyme to become chemically bonded thereto, (2) mixing together an enzyme and a specific substrate to form an enzyme-substrate complex while minimizing the transformation of the substrate to product, (3) contacting the active support member with the enzyme-substrate complex whereby the enzyme component of the enzyme-substrate complex becomes chemically bonded to the support member, and (4) removing the substrate from the enzyme-substrate complex by conventional means, such as water washing.

The above set forth procedure results in commercially useable structure which consists of a support member having chemically bonded thereto an active enzyme.

As used herein the term "substrate" means a substance which undergoes a chemical reaction due to the catalytic action of an enzyme. Likewise, as used herein the term "specific substrate" means a substrate which is a good substrate for a given enzyme.

In addition, as used herein the term "enzyme-substrate complex" means the intermediate which is formed when an enzyme and substrate interact.

The practice of the instant invention can be best understood from a reading of the following detailed example.

EXAMPLE

An arylamine derivative of porous glass (550A, Corning Glass Works) was provided as the insoluble support member. The support member was activated by treatment with a $HCl-NaNO_2$ solution at 0° C. to convert the amine to a diazo structure; this process is described in detail in an article by the inventor and author entitled "Immobilized Pronase" published in *Biochemical and Biophysical Research Communication*, Vol. 44, No. 2, July, 1971 and to the extent necessary for understanding this invention the article is incorporated herein by reference. The insoluble support member consisted of a plurality of glass beads. The enzyme employed was trypsin (Lot TRL2DA from Worthington Biochemical Corporation). The substrate utilized was N-α-benzoyl-L-arginine ethyl ester. The enzyme containing solution was buffered by the use of 0.05 M Tris, pH 8.0, containing 25 mM $CaCl_2$. The enzyme solution (200 ml, 1 mg per ml) and substrate solution (200 ml, $10^{-2}$ M) were placed in separate gradient bottles connected by a T-tube. The remaining opening of the T was connected to a column containing the activated glass beads. The solutions were mixed and pulled through the column by a peristaltic pump. The flow rate was 5 ml per min and the column contained 1 g of activated glass. A temperature range of about 0° to 4° C. was chosen to minimize depletion of substrate and take advantage of the negative enthalpy change for substrate binding. The resultant product, i.e., the chemically bonded (to the support) enzyme-substrate complex, was then subjected to a water washing treatment whereby the substrate material was removed therefrom. The activity of the so-produced immobilized enzyme was about 15 percent.

While washing with water is listed as the preferred material, it will be well known to those having ordinary skill in the art that other relatively inert washing fluids may be used. Subsequently, for the purpose of comparison, unmodified trypsin was immobilized by chemically binding it to a similar type of insoluble support material by conventional means. The activity of the enzyme bonded to the support member without substrate was about 10 percent.

From a review of the foregoing data, it is observed that a given enzyme bonded to a support in the presence of a substrate evidenced an activity which was approximately 50 percent greater than that exhibited by a similar enzyme which was bonded to a similar support without any substrate material being present. In addition, further tests showed that enzyme bonded to a support member in the presence of a substrate according to the teaching of the instant invention exhibited a lesser degree of selectivity than the same enzyme which was bonded to a support member in the absence of a substrate; in other words, the enzyme would act on a greater number of chemical species than the enzyme bound without substrate.

The support member used in the practice of the instant invention can be any material capable of reacting with an enzyme so as to cause the enzyme to become chemically bonded thereto. Among those organic support materials suitable for the practice of the instant invention are carbohydrates, vinyl polymers, amino acid polymers, derivatives of amino acid polymers, nylon, polystyrene structures, and phenol-formaldehyde resins. In addition, among those inorganic supports suitable for the practice of the instant invention are porous glass (arylamine derivatives of porous glass), nickel screen, and alumina-silicate structures. Certain of the foregoing support materials are active in and of themselves and do not require an activation treatment. However, others require activation treatments which are well known in the art and accordingly will not be discussed herein. The foregoing list of suitable supports is not exclusive and is only set forth herein by way of example.

The preferred support for the practice of the instant invention is arylamine porous glass. The method of rendering such a product active is discussed hereinabove and will not now be discussed in detail.

While the instant invention has been described with relation to the use of trypsin as the enzyme to be immobilized, it will be appreciated by those in the art that the instant invention is applicable to other enzymes which are chemically bondable to various support members.

Likewise, while the instant invention has been described in particularity with regard to the use of N-α-benzoyl-L-arginine ethyl ester, as the substrate, it will be readily appreciated by those skilled in the art that other substrate materials may be utilized in the practice of the instant invention.

As pointed out hereinbefore, it is critical to the practice of the instant invention that an enzyme-substrate complex be formed in a manner such that a minimum amount of transformation of the substrate to product occurs. A specific means of accomplishing this is set forth in the above detailed description of the practice of the invention.

It will be apparent that the formation of the enzyme-substrate complex should be accomplished under optimum conditions. For example, it is well known that a given enzyme will interact most efficiently with a given substrate at a certain critical pH. Accordingly, when mixing the enzyme solution with the substrate solution pH should be properly regulated.

In addition, it is to be noted that when forming the enzyme-substrate complex, the enzyme must be saturated with the substrate in order to realize the maximum advantages afforded by the practice of the invention. The invention will operate as indicated where the substrate is not present at saturating concentrations however, the degree of operability will be reduced with less than saturating concentrations.

It will be appreciated by those skilled in the art that other techniques of mixing the enzyme and substrate together while minimizing the transformation of the substrate to product can be utilized in the practice of the instant invention.

Immobilized enzymes produced according to the teachings of the instant invention find application in such processes as cheese making, beer chill proofing and starch hydrolysis.

While there have been described what are at present considered to be the preferred embodiments of this invention, it will be obvious to those skilled in the art that various changes and modifications may be made therein without departing from the spirit and scope of the invention as hereinafter claimed.

What is claimed is:

1. A method of immobilizing an enzyme comprising:
    providing an activated support member which is capable of reacting with an enzyme to cause said enzyme to become chemically bonded thereto;
    in sequence, (1) mixing an enzyme and a substrate and thereby forming an enzyme-substrate complex and (2) contacting said activated support member with the enzyme-substrate complex, said support member being maintained in activated condition prior to contact with the complex by preventing its contact with reactive materials, whereby said enzyme moiety of said enzyme-substrate complex becomes chemically bonded to said support member.

2. The method of claim 1 wherein after said enzyme of said enzyme-substrate complex is chemically bonded to said support member said substrate is removed from said enzyme-substrate complex.

3. The method of claim 2 wherein said substrate is removed by subjecting said enzyme-substrate complex to a washing treatment.

4. The method of claim 1 wherein said support member is selected from the group consisting of carbohydrates, vinyl polymers, amino acid polymers, derivatives of amino acid polymers, nylon, polystyrene, phenol-formaldehyde resins, and mixtures thereof.

5. The method of claim 1 wherein said support member is selected from the group consisting of porous glass, nickel screen and alumina-silicate structures.

6. The method of claim 5 wherein said support member is an arylamine derivative of porous glass.

7. The method of claim 6 wherein said arylamine derivative of porous glass is obtained by reacting an arylamine containing glass with a HCl-NaNO$_2$ solution.

8. The method of claim 1 wherein said support member comprises a plurality of glass beads.

9. The method of claim 1 wherein said enzyme-substrate complex is formed by mixing together said enzyme and said substrate in such a manner that said enzyme is saturated with said substrate.

10. The method of claim 1 wherein after said enzyme of said enzyme-substrate complex is chemically bonded to said support member said substrate is removed from said enzyme-substrate complex.

11. The method of claim 10 wherein said substrate is removed by subjecting said enzyme-substrate complex to a washing treatment.

12. A method for immobilizing an enzyme by bonding to an active solid support member, which consists essentially of premixing an enzyme with an effective amount of a solution of enzyme-complexing substrate material to obtain an enzyme-substrate complex premixture;

contacting the premixture with an active solid support member to effect reaction of the enzyme with the support member; said support member being maintained in activated condition prior to contact with the complex by preventing its contact with reactive materials; and removing the substrate material with an inert liquid to obtain a bonded enzyme having substantially greater enzymic activity than directly bonded enzyme.

13. The method of claim 12 wherein the solid support member comprises porous glass treated to provide a diazo structure, the enzyme consists essentially of trypsin, the complexing substrate consists essentially of N-α-benzoyl-L-arginine ethyl ester, and wherein the enzyme-substrate complex premixture is contacted with the solid support member at about 0° to 4°C.

14. An immobilized enzyme made according to the method of claim 12.

15. An immobilized enzyme made according to the method of claim 13.

16. The method of claim 12 wherein the amount of substrate is sufficient to substantially saturate the enzyme in the complex premixture.

* * * * *